United States Patent [19]

Rezuke et al.

[11] Patent Number: 5,582,865

[45] Date of Patent: Dec. 10, 1996

[54] NON-WOVEN FILTER COMPOSITE

[75] Inventors: Robert W. Rezuke, N. Grafton, Mass.; Devon A. Kinkead, Providence, R.I.

[73] Assignee: Extraction Systems, Inc., Woonsocket, R.I.

[21] Appl. No.: 180,529

[22] Filed: Jan. 12, 1994

Related U.S. Application Data

[63] Continuation of Ser. No. 807,151, Dec. 13, 1991, abandoned, which is a continuation-in-part of Ser. No. 283,318, Dec. 12, 1988, abandoned.

[51] Int. Cl.$^6$ .............................. B05D 1/12; B05D 1/24; B05D 1/40; B05D 5/00
[52] U.S. Cl. ..................... 427/244; 427/180; 427/185; 427/346; 427/366
[58] Field of Search ................................ 427/244, 366, 427/346, 180, 557, 559, 185, 184, 374.4

[56] References Cited

U.S. PATENT DOCUMENTS

| | | |
|---|---|---|
| 1,585,113 | 5/1926 | Robert . |
| 3,019,127 | 1/1962 | Czerwonka et al. .................. 427/184 |
| 3,170,808 | 2/1965 | Almy et al. . |
| 3,196,871 | 7/1965 | Hormats et al. . |
| 3,220,015 | 11/1965 | Shannon ................................. 161/149 |
| 3,226,251 | 12/1965 | Norton et al. ........................ 427/244 |
| 3,294,572 | 12/1966 | Piccione et al. . |
| 3,364,062 | 1/1968 | Mitchell et al. ...................... 427/559 |
| 3,375,933 | 4/1968 | Rodman . |
| 3,381,454 | 5/1968 | Sponsel . |
| 3,525,378 | 8/1970 | Root . |
| 3,545,997 | 12/1970 | Hochberg ............................. 427/559 |
| 3,690,852 | 9/1972 | Smith et al. . |
| 3,697,347 | 10/1972 | Lebruann . |
| 3,779,244 | 12/1973 | Weeks, Jr. et al. . |
| 3,800,516 | 4/1974 | Paluch . |
| 3,870,495 | 3/1975 | Dixson et al. . |
| 3,912,567 | 10/1975 | Schwartz . |
| 3,925,021 | 12/1975 | Yoshino et al. . |
| 3,995,005 | 11/1976 | Teller . |
| 3,998,988 | 12/1976 | Shimomai et al. ................... 428/400 |
| 4,007,301 | 2/1977 | DeMartino ............................ 427/244 |
| 4,011,067 | 3/1977 | Carey, Jr. . |
| 4,075,282 | 2/1978 | Storp et al. .......................... 423/230 |
| 4,081,501 | 3/1978 | Muther . |
| 4,132,650 | 1/1979 | Kirsch et al. . |
| 4,160,059 | 7/1979 | Samejima . |

(List continued on next page.)

FOREIGN PATENT DOCUMENTS

| | | |
|---|---|---|
| 88225 | 11/1895 | Germany . |
| 0034475 | 3/1979 | Japan . |
| 54-34475 | 3/1979 | Japan .......................... 264/DIG. 48 |
| 0262537 | 11/1986 | Japan . |
| 61-262537 | 11/1986 | Japan . |
| 2-126912 | 5/1990 | Japan . |
| 433186 | 8/1935 | United Kingdom . |
| 2005016 | 9/1978 | United Kingdom . |
| 2013102 | 8/1979 | United Kingdom . |
| 2077141 | 4/1981 | United Kingdom . |
| WO90/05549 | 5/1990 | WIPO . |

OTHER PUBLICATIONS

Devon A. Kinkead, Pleated DPCC–based absorbers: New technology for air purification, Ashrae Journal Nov. 1990
Slade et al., "Utilization of Established Air Pollution Monitoring Networks in Ontario Following Nuclear Incidents", Radiation and Industrial Safety Branch Chalk River Nuclear Laboratories, Apr. 1988.
Devon Kinkead., "The Incorporation and Use of Reagent Impregnated Activated Carbons in Nonwoven Webs", American Filtration Society, Mar. 1988.

*Primary Examiner*—Diana Dudash
*Attorney, Agent, or Firm*—Fish & Richardson P.C.

[57] ABSTRACT

A method of making a high efficiency, low pressure drop, adsorptive, non-woven filter composite is disclosed, comprising a high surface area chemically impregnated adsorbent, and a non-woven carrier material; and a method for forming said composite comprising dry application of the chemically impregnated adsorbent to the non-woven carrier material which is then heated and calendared with or without a cover sheet.

26 Claims, 5 Drawing Sheets

U.S. PATENT DOCUMENTS

| | | | |
|---|---|---|---|
| 4,171,410 | 10/1979 | Frob | 427/244 |
| 4,188,960 | 2/1980 | Morie et al. | |
| 4,201,838 | 5/1980 | Goldberg | 429/145 |
| 4,204,011 | 5/1980 | Tanabe et al. | 427/346 |
| 4,215,682 | 8/1980 | Kubik et al. | |
| 4,225,642 | 9/1980 | Hirawaka | |
| 4,277,266 | 7/1981 | Dick | 55/381 |
| 4,285,748 | 8/1981 | Booker et al. | |
| 4,315,965 | 2/1982 | Mason et al. | |
| 4,344,775 | 8/1982 | Klein | |
| 4,376,675 | 3/1983 | Perrotta | |
| 4,379,802 | 4/1983 | Weaver et al. | |
| 4,496,415 | 1/1985 | Sprengling | 427/195 |
| 4,530,272 | 7/1985 | Stokes | |
| 4,578,068 | 3/1986 | Kramer et al. | 604/368 |
| 4,578,256 | 3/1986 | Nishino et al. | 423/210 |
| 4,595,575 | 6/1986 | Oeste et al. | |
| 4,643,182 | 2/1987 | Klein | |
| 4,664,683 | 5/1987 | Degen et al. | |
| 4,680,040 | 7/1987 | Gooray et al. | |
| 4,693,173 | 9/1987 | Saiki et al. | |
| 4,696,837 | 9/1987 | Lindner | |
| 4,699,681 | 10/1987 | Kasmark, Jr. et al. | 427/244 |
| 4,699,808 | 10/1987 | Menard et al. | 427/299 |
| 4,704,972 | 11/1987 | Marchand | |
| 4,737,173 | 4/1988 | Kudirka et al. | 55/276 |
| 4,792,491 | 12/1988 | Atkinson et al. | 427/180 |
| 4,793,837 | 12/1988 | Pontius | 427/244 |
| 4,873,914 | 10/1989 | Hirayama | |
| 4,961,974 | 10/1990 | Jones | 428/34.2 |
| 4,983,192 | 1/1991 | von Blücher et al. | 55/387 |
| 4,985,280 | 1/1991 | Scholz et al. | 427/244 |
| 5,030,423 | 7/1991 | Obee et al. | |
| 5,037,624 | 8/1991 | Tom et al. | 423/210 |
| 5,041,104 | 8/1991 | Seal | 604/367 |
| 5,042,997 | 8/1991 | Rhodes | |
| 5,053,064 | 10/1991 | Hama et al. | |
| 5,064,626 | 11/1991 | Johnson et al. | |
| 5,096,477 | 3/1992 | Shinoda et al. | |
| 5,143,752 | 9/1992 | Nakajima et al. | 427/244 |
| 5,165,595 | 11/1992 | Horio et al. | |
| 5,181,819 | 1/1993 | Sakata et al. | |
| 5,213,767 | 5/1993 | Smith et al. | |
| 5,221,573 | 6/1993 | Baigas, Jr. | |
| 5,271,780 | 12/1993 | Baigas, Jr. | |

NON-WOVEN FILTER COMPOSITE

This is a continuation of application Ser. No. 07/807,151, filed Dec. 13, 1991, now abandoned, which was a continuation-in-part of application Ser. No. 07/283,318 filed Dec. 12, 1988, abandoned, both of which are herein incorporated by reference.

FIELD OF THE INVENTION

This invention relates generally to air filters, and more specifically to a non-woven filter composite and a method for forming said composite.

BACKGROUND OF THE INVENTION

In this age of increased air pollution, the removal of chemicals from the air we breathe is a concern of everyone.

Gas phase filtration is commonly accomplished using activated carbon manufactured in various ways. One approach comprises using a carbon/adhesive slurry to glue the carbon to the substrate. The adhesive decreases carbon performance by forming a film on its surface.

A second approach involves carbonizing an organic based web by heating, followed by carbon activation. This material is high cost and has relatively low adsorption capacity.

A third approach involves forming a slurry of carbon powders and fibers into sheets by a process analogous to a wet papermaking process. This material is medium-to-high cost, and has an undesirable high pressure drop. Moreover, chemically impregnated carbon particles cannot be efficiently used in conjunction with an aqueous process, as the aqueous nature of the process either washes away the chemical used to impregnate the carbon, or reacts undesirably with the impregnating chemical rendering it useless. In general, however, filter materials which do not incorporate chemically impregnated adsorbents perform far less effectively than those which do include chemically impregnated adsorbents.

None of these approaches fully achieve the desired properties which provide a cost effective, high efficiency, low pressure drop, adsorptive composite.

SUMMARY OF THE INVENTION

The present invention comprises a cost effective, high efficiency, low pressure drop, adsorptive, non-woven filter composite comprising a high surface area chemically impregnated adsorbent, a non-woven carrier material, and may include a non-woven cover sheet. The invention also contemplates a method for forming said composite comprising dry application of the chemically impregnated adsorbent to the non-woven carrier material, which is then heated and calendared with or without a cover sheet.

In a preferred embodiment of this invention the non-woven carrier material is polyester batting, and the adsorbent is usually activated carbon, which can be chemically impregnated and which retains its reactive and adsorptive capacity.

The dry processing of the non-woven polyester batting allows for even distribution of adsorbent particles throughout the depth of the polyester batting. This provides an increased bed depth at a very low pressure drop, which is highly desirable since a twofold increase in bed depth can increase the filter's breakthrough time (time to failure) fourfold when using these thin fabric based carbon beds.

Furthermore, less carbon is required to achieve superior results than has been used in-filters of the past.

Thus, the invention provides a cost effective, high efficiency, low pressure drop, adsorptive non-woven filter composite, and a method for forming said composite. The novel filter composite is useful for the removal of toxic and other contaminants in an air stream, which contaminants can be gaseous or vaporous. Particulates will also be removed if greater than the pore size of the filter.

DESCRIPTION OF THE DRAWING

Other features and advantages of the invention will be apparent from the following description in conjunction with the accompanying drawing, wherein.

DETAILED DESCRIPTION OF THE INVENTION

The method and apparatus of this invention are described with reference to the drawings.

Figure 1:
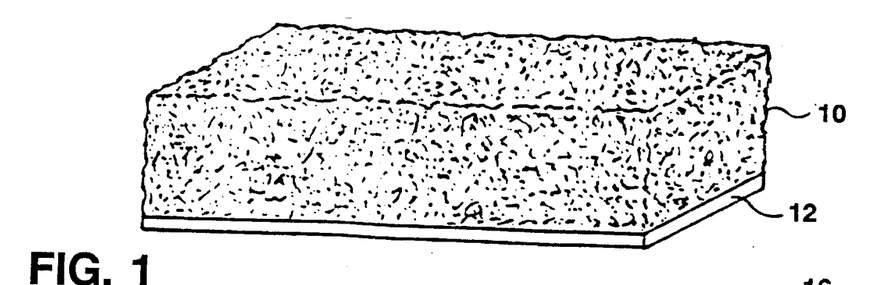
FIG. 1 is a perspective view of the apparatus of this invention before heating and calendaring.

As shown in FIG. 1, the dense non-woven backing is preferably a polyester batting with a denier in the range of about 15 denier which is needled, thereby increasing its density by concentrating and reducing the initial thickness to a final thickness of approximately 0.25 inch. This material is then spray bonded to a loose non-woven polyester batting of approximately 6 denier having a thickness of approximately 1 inch. The resulting polyester batting has two distinct layers and a thickness of approximately 0.8 inch.

Alternatively, the non-woven carrier may comprise a polyester batting which is needled on one side thereby forming a single polyester batting having a dense layer on one side and a total thickness of about 0.8 inch.

Figure 2:
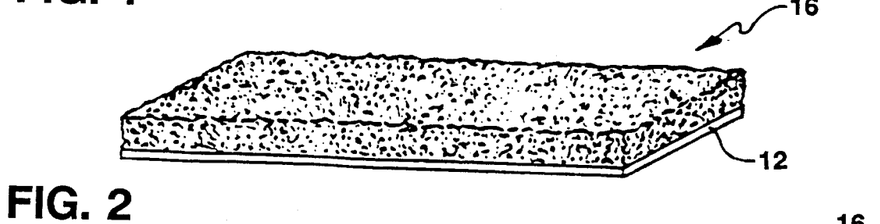
FIG. 2 is a perspective view of the apparatus of this invention after heating and calendaring.

The polyester batting 10, 12, is then heated and calendared to provide the compressed structure of FIG. 2.

Figure 2A:
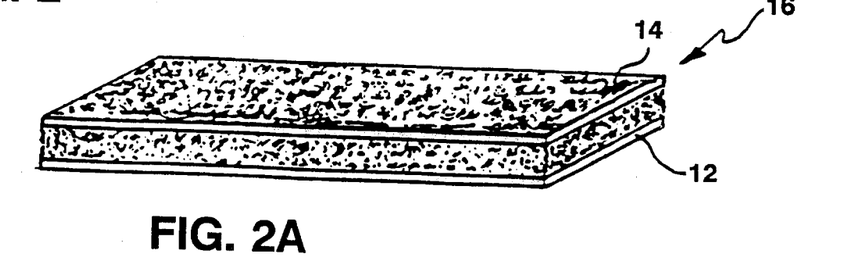
FIG. 2A is a perspective view of the apparatus of this invention after heating and calendaring with a cover sheet.
Figure 2B:
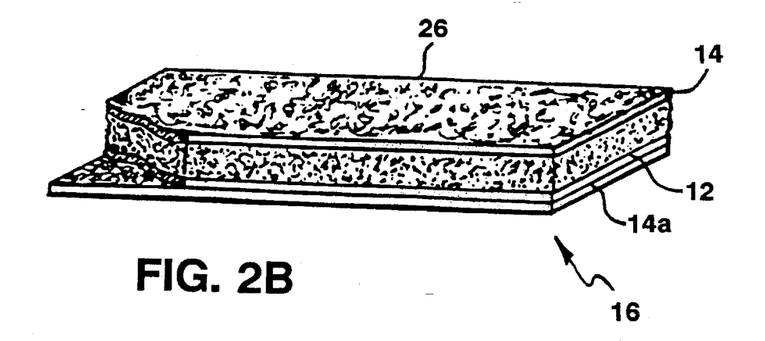
FIG. 2B is a perspective view of the apparatus of this invention after heating and calendaring with a cover sheet on both sides of the composite.

The structure of FIG. 2 can be used directly in this form as the composite filter element. If desired, the composite 16, can be employed with a cover sheet 14, provided on the surface of batting 10, opposite to the backing 12, as shown in FIG. 2A. Alternatively, a second cover sheet 14a, can be provided over the backing layer 12, as shown in FIG. 2B. The cover sheet can be a filtering or non-filtering non-woven polyester, polyamide or polypropylene material or other similar materials. If the cover sheet is a filtering material, it serves to provide some filtering of the air entering the composite structure for removal of particulate materials in the air stream. The cover can also serve to retain the carbon within the batting 10. The cover sheet can also be of a material such as polypropylene operative as a vapor and/or a moisture barrier.

Figure 3:
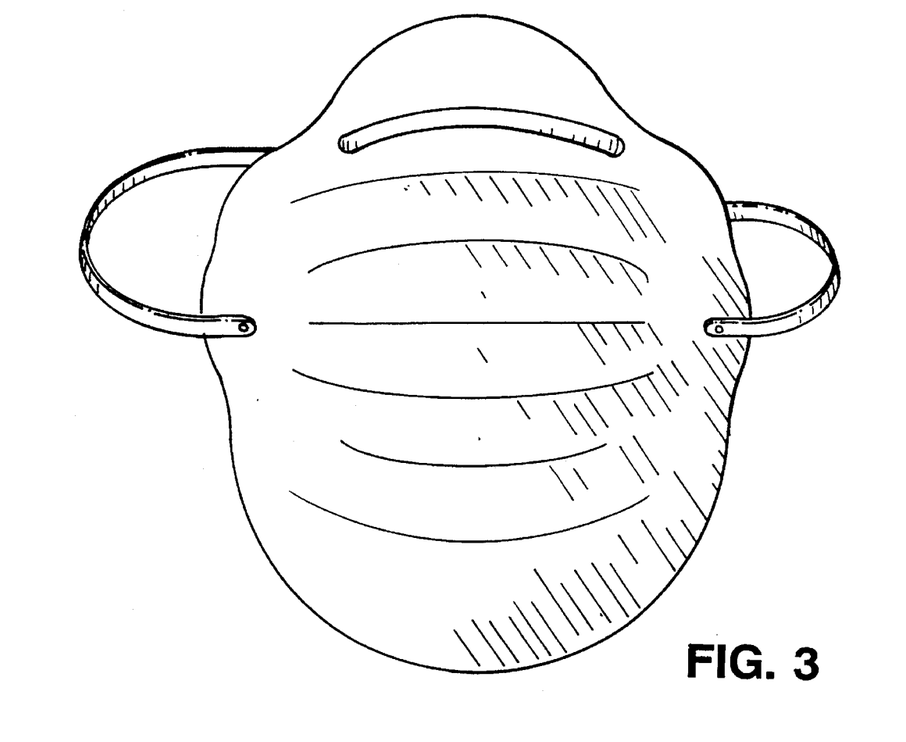
FIG. 3 is a front view of the apparatus of this invention molded into a disposable self-contained face mask filter.

The composite structure 16, in any of the embodiments illustrated, can be thermally molded into various intended shapes, such as a disposable self-contained face mask filter, as shown in FIG. 3.

The composite 16, can be contained within any suitable container or frame work for installation in an intended position for filtering operation, typically in the form of a removable or replaceable filter element. For many purposes, it is preferable to increase the surface area of the filter material exposed to an incident air flow, and for this purpose the composite can be embossed and then pleated to provide the increased surface area. The embossment further acts as a spacing mechanism which maintains an aerodynamic positive to the air flow which reduces air flow resistance and subsequent operating costs.

Figure 4:
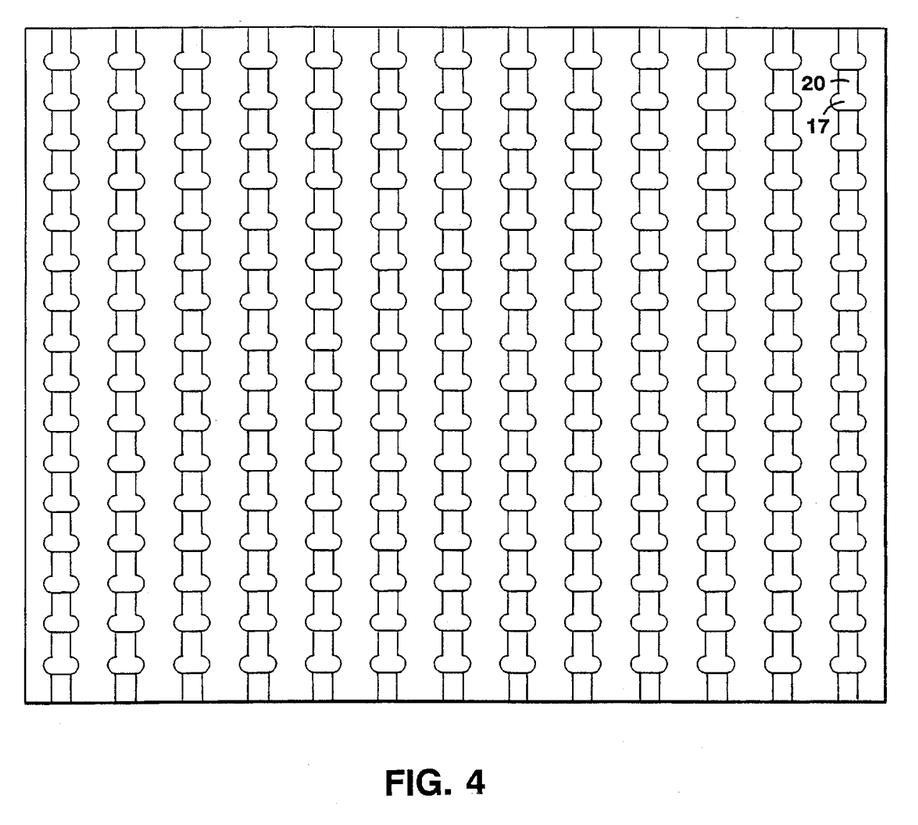
FIG. 4 is a front or back view of the apparatus of this invention in a square or rectangular containment structure showing the creases of the pleated and embossed structure.
Figure 4A:
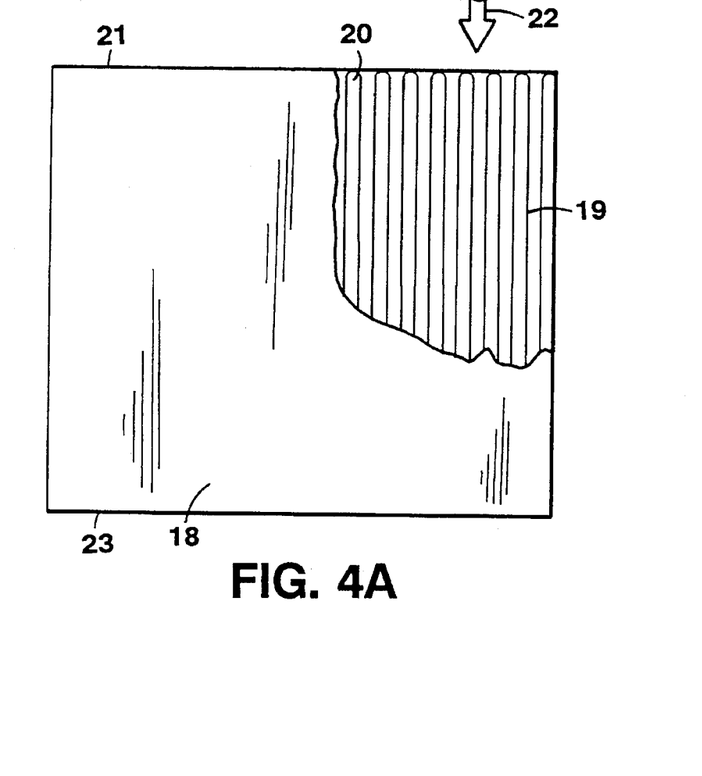
FIG. 4A is a top view of the apparatus of this invention showing its pleated and embossed structure.

One embodiment is shown in FIGS. 4 and 4A, in which the composite material is embossed and then pleated into an accordionlike structure 19, contained within a square or rectangular container 18, having a front 21, and back 23, which are open to an air stream shown by arrow 22. The embossing 17 and pleating 20, are substantially perpendicular to the air flow. FIG. 4 shows the structure in a front or back view, while FIG. 4A shows a cutaway top view of the structure.

Figure 4B:
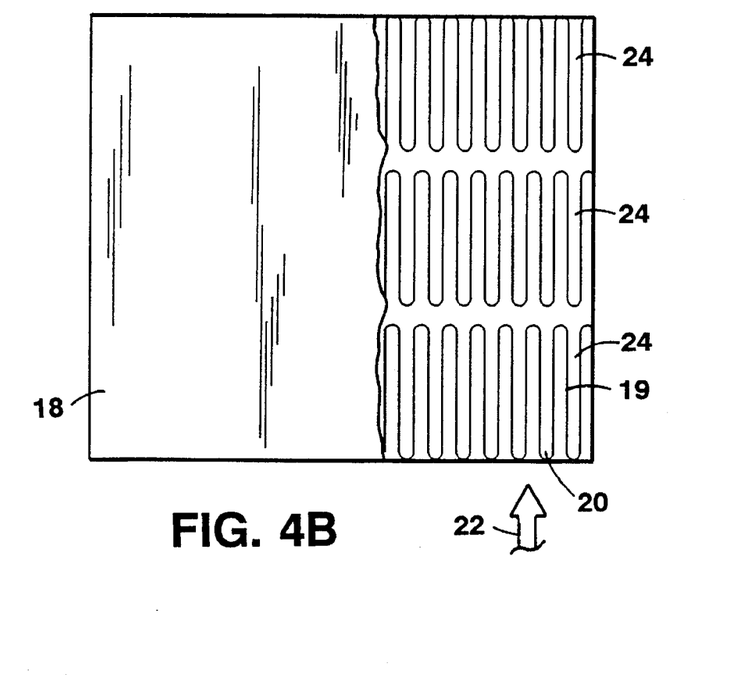
FIG. 4B is a top view of the apparatus of this invention with a high first pass efficiency multi-pleat pack panel filter in a square or rectangular containment structure.

An alternative embodiment is shown in FIG. 4B wherein a plurality of pleated composite elements 24, are sequentially disposed within container 18, to provide a multi-stage filter through which the air can pass. As in the above embodiment, the pleats 20, of the elements 24, are substantially perpendicular to the direction of air flow 22.

Figure 5:
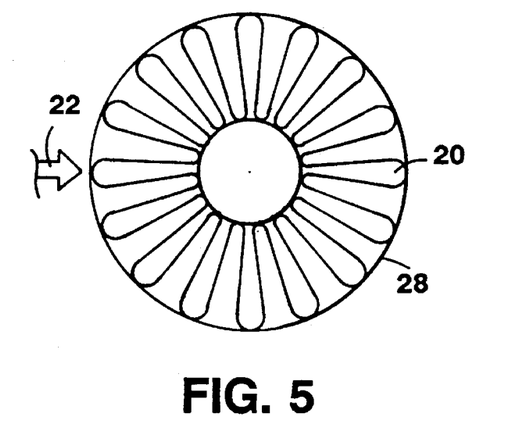
FIG. 5 is a top view of the apparatus of this invention in a radially pleated cylindrical containment structure.
Figure 5A:
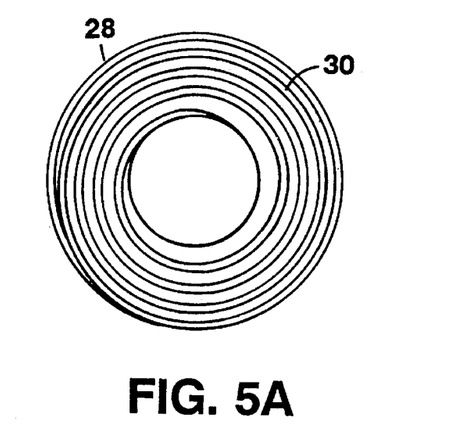
FIG. 5A is top view of the apparatus of this invention in a media-wrapped cylindrical filter.

A further embodiment is shown in FIG. 5, wherein the composite structure 16, is disposed in a cylindrical configuration and retained within a cylindrical container 28. The pleats 20, are as described above, substantially perpendicular to a radially directed air flow. A further embodiment is shown in FIG. 5A wherein the composite structure is wound in a spiral configuration 30, contained within a generally cylindrical container 28.

In a preferred embodiment, adsorbent particles are evenly distributed throughout the polyester batting. An example of an adsorbent particle includes but is not limited to activated carbon which is chemically impregnated and retains its reactive and adsorptive capacity as a result of the dry processing.

Alternatively, the adsorbent particles may be ion exchange resins.

Overall, the dry processing of the non-woven polyester batting, which includes the combination of the fluidized bed carbon deposition process, the inherent stratification of the batting's density, and the even distribution of the carbon particles as well as stratification of the carbon particle size, allows for a fabric architecture having an increased bed depth at a very low pressure drop, which is highly desirable due to its high first pass efficiency coupled with its low operating cost.

The term "efficiency" as employed herein is defined by the formula $$X-Y/X$$

wherein X is the upstream concentration of pollutant, and Y is the downstream concentration of pollutant.

In an improved method of the invention (FIG. 6), after the adsorbent particles 60 are poured onto a polyester batting 62 from a fluidized bed 64, the batting 62 is agitated using a roll bar 66 which agitates in a direction which is perpendicular to the length of the batting. This agitation insures that the carbon particles 60 ranging in mesh size from 20×50 to 30×140 are evenly stratified throughout the depth of the batting 62. As discussed above, an increased bed depth of adsorbent particles distributed throughout the batting is highly desirable as it increases residence time, increases exposure of the adsorbent particle surfaces, provides a low pressure drop, as well as substantially increasing the lifetime of the filter.

Figure 6:
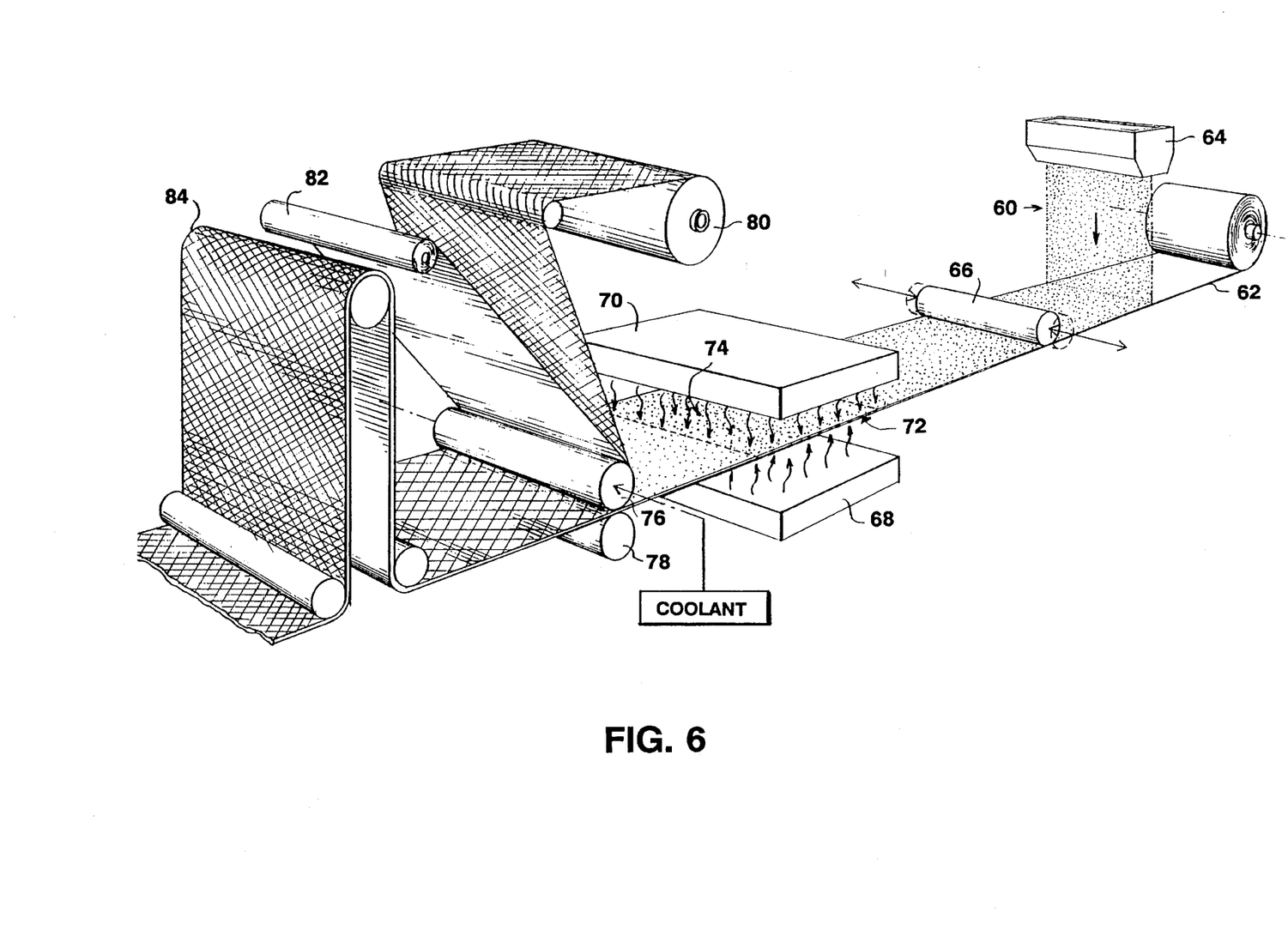
FIG. 6 is a perspective view of the process of the invention.

The adsorbent particles 60 distributed in the batting 62 are then heated, preferably using two zones 68,70 of infrared energy at different wavelengths. In the first zone 68, the wavelength is shorter and is directed toward the dense non-woven backing 72 of the composite to insure that heat energy penetrates deep within the dense backing. In the second zone 70, the wavelength is longer as it is easier for the heat energy to penetrate the loose non-woven surface 74. The batting 62 is heated to an overall average temperature of about 350° F.

The infrared energy causes the adsorbent particles to adhere to the batting at points where the particles contact the batting. This procedure avoids the necessity of raising the temperature of the entire batting to a point at, or near, the melting point of the polyester batting, which could cause the batting to melt and collapse thereby encasing the particles and destroying the their chemical activity.

The batting 62 is then calendared using a pair of calendar rolls 76,78. The first of these rolls 76 can be temperature controlled which allows the heating and calendaring steps to be carried out at a steady temperature of around 110°–115° F., and prevents overheating and subsequent melting of cover sheet and prevents over calendaring of the fabric.

Furthermore, when the temperature controlled roller 76 is used, the pressure at which the batting is calendared can be lowered from 3000–5000 psi to under 1000 psi as a result of the steady temperature maintained during calendaring. Higher calendaring pressures can crush the particles particularly when those particles are chemically impregnated carbon particles, thereby forming dust, which cannot be retained in the filter composite. Therefore, the ability to use lower pressures in the calendaring step is very desirable in preventing the destruction of the carbon particles contained in the batting, and formation of carbon dust.

In addition, a non-woven cover sheet 82, which helps to maintain the carbon in the batting, may be calendared with the batting 62, as discussed above.

If the filter material is to be pleated as discussed earlier, a wire mesh 80 may be calendared with the batting. The wire mesh 80 helps maintain the filter material in a pleated configuration. The presence of the wire mesh 80 in the filter material also enables the filter material to be embossed before pleating. Embossing a material before pleating is a known technique in the industry. The advantages of embossing have been discussed above.

Optionally, the material may be conducted over an upper roller 84 to facilitate cooling the material prior to further processing.

The following examples illustrate the present invention more specifically.

EXAMPLE I

Zinc chloride impregnated activated carbon, approximate mesh size range 20×50 to 30×140, is fluidized on a vibrator tray which spills the carbon into a roller system from which it falls into a non-woven polyester carrier with a loose non-woven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure of approximately 3000–5000 psi. A cover sheet which can be non-filtering or filtering, non-woven material, can be calendared with the batting.

If desired, the composite can be pleated using machines common to the air filter business. The pleated structure may be placed in a containment structure such that the crease of the fold is perpendicular to the air flow. The resulting composite can remove ammonia and low molecular weight amines from an air stream with a low pressure drop.

EXAMPLE II

Iodine impregnated activated carbon, approximate mesh size range 20×50 to 30×140, is fluidized on a vibrator tray which spills the carbon into a roller system from which it falls into a non-woven polyester batting with a loose non-woven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure of approximately 3000–5000 psi. A cover sheet which can be non-filtering or filtering, non-woven material, can be calendared with the batting. If desired, the composite can be pleated as noted in Example I. The resulting composite can remove mercury and organic vapors from an air stream with a low pressure drop.

EXAMPLE III

Bromine impregnated activated carbon, approximate mesh size range 20×50 to 30×140, is fluidized on a vibrator tray which spills the carbon into a roller system from which it falls into a non-woven polyester batting with a loose non-woven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure approximately 3000–5000 psi. A cover sheet which can be non-filtering or filtering, non-woven material, can be calendared with the batting.

If desired, the composite can be pleated as noted above. The resulting composite can remove unsaturated hydrocarbons, such as ethylene, from an air stream with a low pressure drop.

EXAMPLE IV

Transition metal oxides/metal oxide salts/ammonia impregnated activated carbon, commonly referred to as whetlerite carbon, approximate mesh size range 20×50 to 30×140, is fluidized on a vibrator tray which spills the carbon into a roller system from which it falls into a non-woven polyester batting with a loose non-woven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure of approximately 3000–5000 psi. A cover sheet which can be non-filtering or filtering, non-woven material, can be calendared with the batting.

If desired, the composite can be pleated as noted above. The resulting composite can remove arsine, stibine, hydrogen sulfide, cyanogen chloride, hydrogen cyanide, chloropicrin, carbonyl chloride, diethylmethylphosphonate, and formaldehyde from an air stream with a low pressure drop. Protecting this composite with a polypropylene cover sheet allows its use to prevent escape of unpleasant odors from a colostomy bag.

EXAMPLE V

Sodium carbonate impregnated activated carbon, approximate mesh size range 20×50 to 30×140, is fluidized on a vibrator tray which spills the carbon into a roller system from which it falls into a non-woven polyester batting with a loose non-woven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure of approximately 3000–5000 psi. A cover sheet which can be non-filtering or filtering, non-woven material, can be calendared with the batting.

If desired, the composite can be pleated as noted above. The resulting composite can remove acid gases such as hydrogen sulfide, sulfur dioxide, chlorine, nitrogen dioxide, fluorine, and bromine from an air stream with a low pressure drop.

EXAMPLE VI

Sodium chromate impregnated activated carbon, approximate mesh size range 20×50 to 30×140, is fluidized on a vibrator tray which spills the carbon into a roller system from which it falls into a non-woven polyester batting with a loose non-woven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure of approximately 3000–5000 psi. A cover sheet which can be non-filtering or filtering, non-woven material, can be calendared with the batting. If desired, the composite can be pleated as noted above. The resulting composite can remove formaldehyde from an air stream with a low pressure drop.

EXAMPLE VII

Unimpregnated coconut shell activated carbon, approximate mesh size range 20×50 to 30×140, is fluidized on a vibrator tray which spills the carbon into a roller system from which it falls into a non-woven polyester batting with a loose non-woven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure of approximately 3000–5000 psi. A cover sheet which can be non-filtering or filtering, non-woven material, can be calendared with the batting.

If desired, the composite can be pleated as noted above. The resulting composite can remove organic vapors from an air stream with a low pressure drop.

EXAMPLE VIII

Triethylenediamine and or iodine and or potassium iodide(s) impregnated activated carbon, approximate mesh size range 20×50 to 30×140, is fluidized on a vibrator tray which spills the carbon into a roller system from which it falls into a non-woven polyester batting with a loose nonwoven surface attached to a dense non-woven backing. The batting and its contents are then heated to a temperature of approximately 250°–350° F. for 20–30 seconds, and calendared using a 24 inch face, 5 inch diameter pair of calendar rolls, which provide a pressure of approximately 3000–5000 psi. A cover sheet which can be non-filtering or filtering, non-woven material, can be calendared with the batting.

If desired, the composite can be pleated as noted above. The resulting composite can remove organic and inorganic radioiodides from an air stream with a low pressure drop.

EXAMPLE IX

Iodine impregnated activated carbon, approximate mesh size range 20×50 to 30×140, is fluidized on a vibrator tray which spills the carbon into a roller system from which it falls into a non-woven polyester batting with a loose non-woven surface attached to a dense non-woven backing.

The batting is then agitated to cause the carbon particles to be distributed throughout the depth of the batting. The agitation causes the smaller particles to migrate furthest from the batting surface while the larger particles remain nearer the surface thereby providing a stratification of carbon particles throughout the depth of the polyester batting. The batting and its contents are then subjected to two zones of infrared energy for about 30 seconds. The first zone having a shorter wavelength is directed toward the dense non-woven backing. The second zone of infrared energy, having a longer wavelength is directed onto the loose surface of the batting.

The batting was then calendared using a 24 inch face, 5 inch diameter pair of calendar rolls. The first of these rollers is temperature controlled to maintain a steady temperature of 100°–115°F., throughout the heating and calendaring process.

The calendar rolls provide a pressure of approximately 1000 psi. A cover sheet which can be non-filtering or filtering, non-woven material, and a wire mesh can be calendared with the batting.

If desired, the filter material can be embossed by positive and negative embossing as is known in the art. The composite can then be pleated as noted in Example I.

The resulting composite can remove mercury and organic vapors from an air stream having a face velocity of more than 20 linear feet per minute with a low pressure drop.

EXAMPLE X

Tromethamine impregnated activated carbon, approximate mesh size range 20×50 to 30×140, is fluidized on a vibrator tray which spills the carbon into a roller system from which it falls into a non-woven polyester batting with a loose non-woven surface attached to a dense non-woven backing.

The batting is then agitated to cause the carbon particles to be distributed throughout the depth of the batting. The agitation causes the smaller particles to migrate furthest from the batting surface while the larger particles remain nearer the surface thereby providing a stratification of carbon particles throughout the depth of the polyester batting. The batting and its contents are then subjected to two zones of infrared energy for about 30 seconds. The first zone having a shorter wavelength is directed toward the dense non-woven backing. The second zone of infrared energy, having a longer wavelength is directed onto the loose surface of the batting.

The batting is then calendared using a 24 inch face, 5 inch diameter pair of calendar rolls. The first of these rollers is temperature controlled to maintain a steady temperature of 100°–115°F. throughout the heating and calendaring process.

The calendar rolls provide a pressure of approximately 1000 psi. A cover sheet which can be non-filtering or filtering, non-woven material, and a wire mesh can be calendared with the batting.

If desired, the filter material can be embossed by positive and negative embossing as is known in the art. The composite can then be pleated as noted in Example I.

The resulting composite can remove formaldehyde or low molecular weight aldehydes and $NO_2$ from an air stream having a face velocity of more than 20 linear feet per minute with a low pressure drop.

It will further be appreciated that various changes may be made to the invention as set forth above. It will be understood that all matter herein described is to be interpreted as illustrative only and is not to limit the invention.

What is claimed is:

1. A method for forming a vapor absorptive non-woven air filter composite comprising thermo-plastic fibers and adsorptive particles, said composite having a given fiber density, comprising the steps of:

providing a non-woven carrier material having a substantially flat top surface and comprising thermo-plastic fibers of lower fiber density relative to the fiber density of the resultant composite;

under dry conditions, applying adsorbent particles of a range of particle sizes to said top surface of said carrier material, agitating said carrier material until the adsorbent particles penetrate the top surface of the carrier material and become distributed throughout the depth of said carrier material;

thereafter heating said carrier material and applied adsorbent particles; and calendering the heated carrier material with said adsorbent particles distributed therethrough;

wherein said heating and calendering steps are performed for a period of time and under a pressure selected to be sufficient for said adsorbent particles to become retained within said heated and calendered carrier material to form a calendered composite having an open fibrous structure of said given fiber density with the surfaces of said distributed adsorbent particles being substantially exposed for contact with air passing through said calendered composite, said resulting non-woven air filter composite being characterized by a pressure drop sufficient for use as an air filter.

2. A method for forming a vapor adsorptive non-woven air filter composite comprising thermo-plastic fibers and adsorptive particles, said composite having a given fiber density, comprising the steps of:

providing a non-woven carrier material having a substantially flat top surface and comprising thermo-plastic fibers of lower fiber density relative to the fiber density of the resultant composite;

under dry conditions, applying adsorbent particles of a range of particle sizes to said top surface of said carrier material;

agitating said carrier material until the adsorbent particles penetrate the top surface of the carrier material and become distributed through the depth of said carrier material;

heating said carrier material to a temperature below the melting point of the fibers of said carrier material; and calendering the heated carrier material with said adsorbent particles distributed therethrough;

wherein said calendering step is performed under a pressure selected to be sufficient for said adsorbent particles to become retained within said heated and calendered carrier material to form a calendered composite having an open fibrous structure of said given fiber density with the surfaces of said distributed adsorbent particles being substantially exposed for contact with air passing through said calendered composite, said resulting non-woven air filter composite being characterized by a pressure drop sufficient for use as an air filter.

3. The method of claim 1 or 2, further comprising the step of applying a wire mesh to the carrier material prior to said calendering step.

4. The method of claim 3, further comprising the step of embossing said carrier material after said calendering step.

5. The method of claim 4, further comprising the step of pleating said carrier material after said embossing step.

6. The method of claim 1 or 2 wherein said non-woven carrier material comprises a non-woven batting having a non-woven top layer surface attached to a relatively higher fiber density non-woven backing layer.

7. The method of claim 1 or 2 wherein said adsorbent particles are chemically impregnated carbon particles.

8. The method of claim 7 wherein said carbon particles are impregnated with chemicals selected from the group consisting of copper chloride, iodine, bromine, transition metal oxides and salts thereof, sodium carbonate, sodium chromate, triethylenediamine, tromethamine, potassium hydroxide and potassium iodide.

9. The method of claim 1 or 2 wherein said adsorbent particles are ion exchange resins.

10. The method of claim 1 or 2, wherein said calendering step includes using at least one calender roll which is temperature controlled.

11. The method of claim 1 or 2 wherein said adsorbent particles are non-impregnated activated carbon particles.

12. The method of claim 1 or 2 wherein said range of particle sizes lies between about 20 and 140 mesh.

13. The method of claim 1 or 2 wherein said step of agitating said carrier material comprises agitating said carrier material in a direction which is both perpendicular to the direction of travel of the carrier material and along said substantially flat surface of said carrier material.

14. The method of claim 1 or 2 further comprising the step of applying a cover sheet to said open surface of the carrier material.

15. The method of claim 14 further comprising the step of applying a second cover sheet to a second surface of said carrier material, said second surface being opposite said open surface.

16. The method of claim 1 or 2 wherein said step of applying adsorbent particles comprises the step of fluidizing said adsorbent particles on a vibrator tray.

17. The method of claim 16 further comprising the step of spilling said adsorbent particles from said vibrator tray into a roller system from which said particles fall onto said carrier material.

18. The method of claim 2 wherein the non-woven carrier material that is provided comprises polyester fibers.

19. The method of claim 1 or 2 wherein the resulting air filter composite that is formed has a thickness of about 0.8 inches.

20. The method of claim 2 wherein said heating step is performed after said applying and agitating steps.

21. The method of claim 6 wherein said top layer is thicker along the depth dimension of said carrier material than said backing layer.

22. The method of claim 6 wherein said backing layer comprises a needle-punched layer.

23. The method of claim 13 wherein said carrier material is agitated using a roll bar.

24. The method of claim 2 wherein said thermo-plastic fibers are formed of polyester and during said heating step said polyester fibers are heated to a temperature in the range of 250°–350° F.

25. The method of claim 1 or 2 wherein the thermoplastic fibers of said non-woven carrier material are of uniform material composition.

26. The method of claim 1 or 2 wherein said calendering step is carried out at a calendering pressure of 3000–5000 psi.

\* \* \* \* \*